US007803192B2

(12) United States Patent
Oh et al.

(10) Patent No.: US 7,803,192 B2
(45) Date of Patent: Sep. 28, 2010

(54) ARTIFICIAL INTERVERTEBRAL DISC

(75) Inventors: YoungHoon Oh, Montville, NJ (US); Aaron Markworth, Saddle Brook, NJ (US); Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 443 days.

(21) Appl. No.: 11/831,027

(22) Filed: Jul. 31, 2007

(65) Prior Publication Data

US 2009/0036987 A1 Feb. 5, 2009

(51) Int. Cl.
*A61F 2/44* (2006.01)
(52) U.S. Cl. .................... 623/17.16; 623/17.11
(58) Field of Classification Search ......... 606/248–249; 623/17.11–17.16
See application file for complete search history.

(56) References Cited

U.S. PATENT DOCUMENTS

| 4,309,777 | A | 1/1982 | Patil |
| 4,759,769 | A | 7/1988 | Hedman et al. |
| 4,946,378 | A | 8/1990 | Hirayama et al. |
| 5,071,437 | A | 12/1991 | Steffee |
| 5,458,643 | A | 10/1995 | Oka et al. |
| 5,676,701 | A | 10/1997 | Yuan et al. |
| 5,893,889 | A | 4/1999 | Harrington |
| 6,162,252 | A | 12/2000 | Kuras et al. |
| 6,402,785 | B1 | 6/2002 | Zdeblick et al. |
| 6,533,818 | B1 | 3/2003 | Weber et al. |
| 6,607,558 | B2 | 8/2003 | Kuras |
| 6,626,943 | B2 | 9/2003 | Eberlein et al. |
| 6,645,248 | B2 | 11/2003 | Casutt |
| 6,656,224 | B2 | 12/2003 | Middleton |
| 6,706,068 | B2 | 3/2004 | Ferree |
| 6,723,127 | B2 | 4/2004 | Ralph et al. |
| 6,960,232 | B2 | 11/2005 | Lyons et al. |
| 6,996,931 | B1 | 2/2006 | Ratte |
| 2005/0251260 | A1* | 11/2005 | Gerber et al. ............ 623/17.13 |

\* cited by examiner

*Primary Examiner*—Eduardo C Robert
*Assistant Examiner*—Christina Negrelli
(74) *Attorney, Agent, or Firm*—Rahman LLC

(57) ABSTRACT

An artificial intervertebral disc and method of attaching the disc to vertebral bodies includes a plurality of separate structural members arranged in a stacked configuration, wherein each structural member comprises a female cavity having a unique size compared with the female cavities of the other structural members, wherein a top and middle structural member comprise male bodies defined by outer edges of the respective female cavities of the top and middle structural members, wherein the male body of the top structural member is dimensioned and configured to sit in the female body of the middle structural member, wherein the male body of the middle structural member is dimensioned and configured to sit in the female body of a bottom structural member, and wherein each of the top and bottom structural member comprise at least one projecting member outwardly extending therefrom.

20 Claims, 7 Drawing Sheets

Section A-A

Section A-A

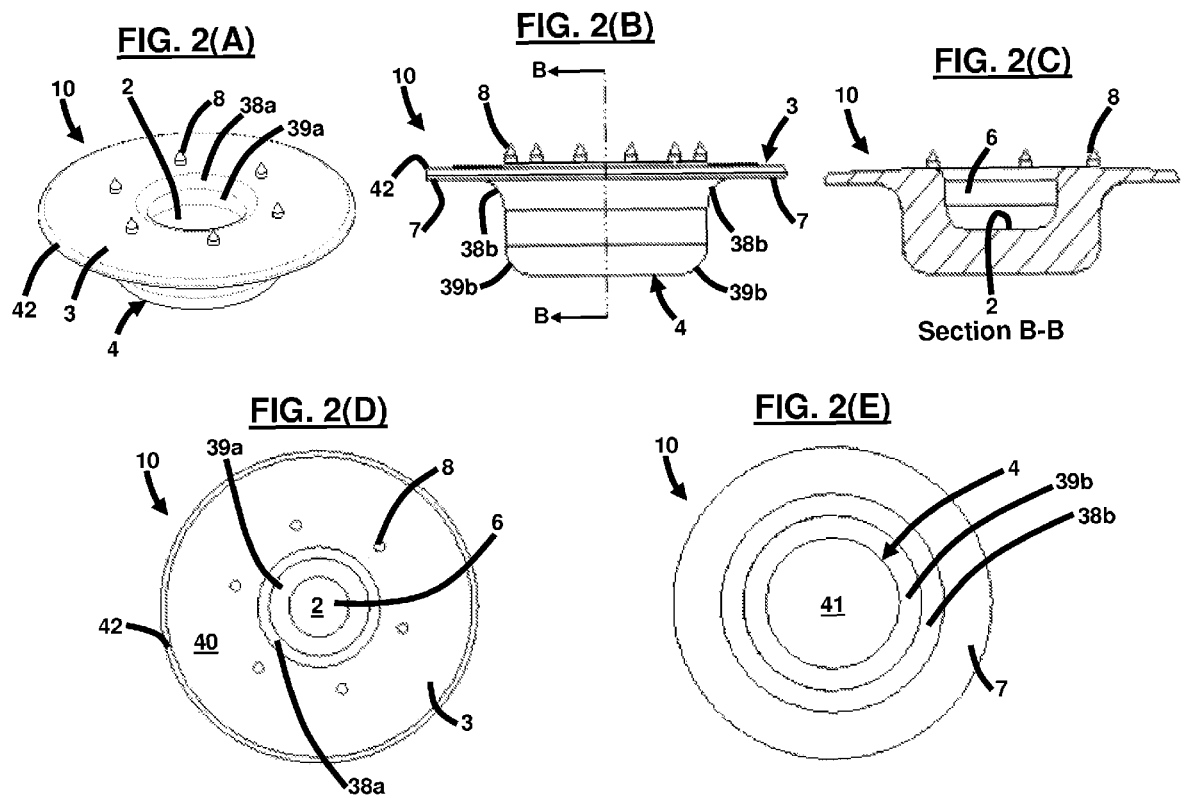

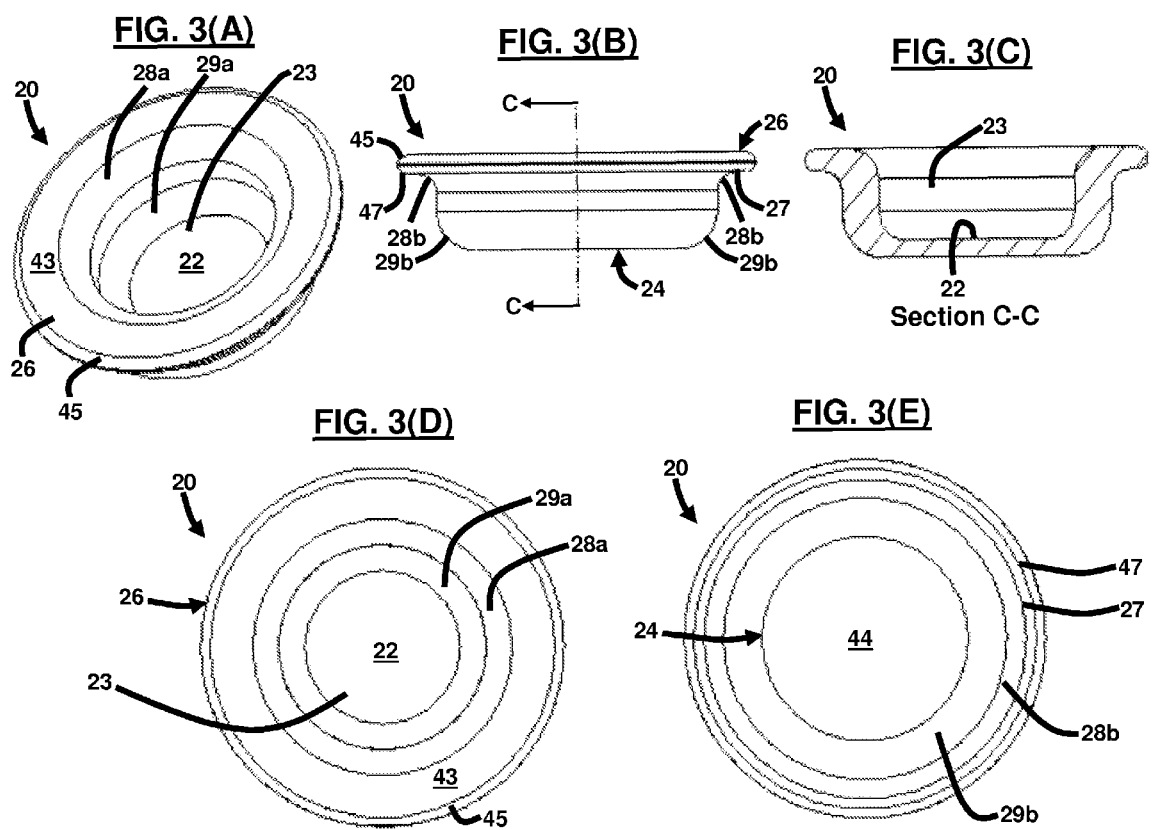

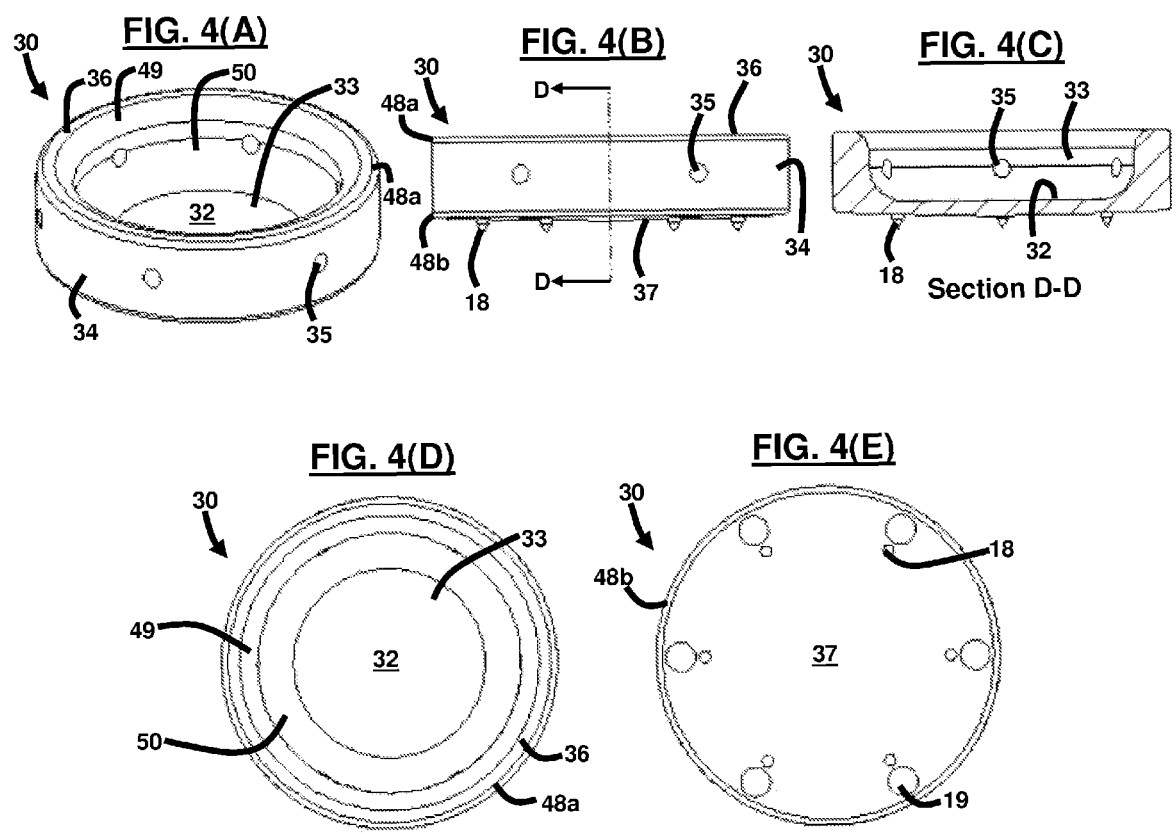

FIG. 5

ATTACHING AN UPPER SURFACE OF A SUPERIOR BODY COMPONENT TO A SUPERIOR VERTEBRAL BODY. — 51

↓

ATTACHING A BOTTOM SURFACE OF AN INFERIOR BODY COMPONENT TO AN INFERIOR VERTEBRAL BODY. — 52

↓

INSERTING A LOAD-BEARING COMPONENT IN BETWEEN THE SUPERIOR BODY COMPONENT AND THE INFERIOR BODY COMPONENT. — 53

ARTIFICIAL INTERVERTEBRAL DISC

BACKGROUND

1. Technical Field

The embodiments herein generally relate to prosthetic devices, and, more particularly, to an artificial intervertebral disc used for stabilizing vertebral bodies.

2. Description of the Related Art

The human spine contains multiple flexible levels of joints comprising adjacent vertebral bones. The joints comprise two-part intervertebral discs consisting of a nucleus and an annulus. The joint system allows for both motion and stabilization of the spinal column with the disc providing motion and cushioning to the joint. The joint is subjected to varying loads, which, over time, can result in mechanical breakdown (i.e., fatigue and fracture, etc.) of the disc (i.e., disc degeneration) due to a variety of reasons including aging, damage due to excessive loading, trauma, and other anatomical issues. Severe joint degeneration and failure may require medical intervention including implanting artificial intervertebral discs to cure the deficiencies of the spinal column.

Such a surgical procedure is complex and generally involves fusing the damaged section of the spinal column into a single mass of bone. While this treatment generally alleviates the pain associated with damaged joints the surgical fusion may result in unintended complications including the body rejecting the prosthesis, incorrect alignment, or mechanical breakdown of the artificial discs themselves. Furthermore, because one level of the spine is operatively connected to the other adjacent levels of the spine, biomechanically altering one level may eventually alter the alignment of the adjacent levels requiring future surgery.

Accordingly, it is one objective of intervertebral disc replacement to provide a prosthetic disc that combines both stability to support the high loads of the patient's vertebrae and flexibility to provide the patient with sufficient mobility and proper spinal column load distribution so as to not negatively impact the adjacent levels. Various types of artificial intervertebral discs have been developed for replacing a part or all of a removed disc. However, most artificial discs used as a substitute to an intervertebral disc typically only allow and control one of two types of motion: (i) rigid rotation/translation, or (ii) soft uncontrolled spring/damping. Therefore, there remains a need for a novel artificial intervertebral disc capable of controlling both types of motion.

SUMMARY

In view of the foregoing, an embodiment provides an artificial intervertebral disc comprising a first body component having a first body upper surface, the first body component comprising a flanged outer periphery; at least one first body projection member extending outwardly from the first body upper surface; and a first bowl region connected to the flanged outer periphery of the first body component, wherein the first bowl region comprises a first body cavity extending inwardly from the first body upper surface. The disc further comprises a second body component having a second body upper surface, the second body component comprising a flanged outer periphery; and a second bowl region connected to said flanged outer periphery of said second body component, wherein said second bowl region comprises a second body cavity extending inwardly from the second body upper surface. The disc further comprises a third body component having a third body upper surface and a third body bottom surface, the third body component comprising a third body cavity extending inwardly from the third body upper surface; at least one third body projection member outwardly extending from the third body bottom surface, wherein the first bowl region is dimensioned and configured to fit in the second body cavity, and wherein the second bowl region is dimensioned and configured to fit in the third body cavity.

Preferably, each of the at least one first body projection member and the at least one third body projection member are adapted to respectively anchor into oppositely positioned vertebral bodies. Moreover, the third body component may further comprise a sidewall defining an outer boundary of the third body cavity, and wherein the sidewall comprises at least one hole extending through an entire thickness of the sidewall. Also, the third body bottom surface may comprise at least one dimple extending inwardly from the third body bottom surface. Furthermore, the second body component may comprise flexible material. Additionally, each of the first body component and the third body component may comprise metallic material. The artificial disc may further comprise a gap between a bottom surface of the second body cavity and a top surface of the third body cavity when the second body component is seated in the third body component.

Another embodiment provides an artificial intervertebral disc comprising a plurality of separate structural members arranged in a stacked configuration, wherein each structural member comprises a female cavity having a unique size compared with the female cavities of the other structural members, wherein a top and middle structural member comprise male bodies defined by outer edges of the respective female cavities of the top and middle structural members, wherein the male body of the top structural member is dimensioned and configured to sit in the female body of the middle structural member, wherein the male body of the middle structural member is dimensioned and configured to sit in the female body of a bottom structural member, and wherein each of the top and bottom structural member comprise at least one projecting member outwardly extending therefrom.

Preferably, each at least one projection member of the top and bottom structural members are adapted to respectively anchor into oppositely positioned vertebral bodies. Moreover, the bottom structural member may further comprise a sidewall defining an outer boundary of the female cavity of the bottom structural member, and wherein the sidewall comprises at least one hole extending through an entire thickness of the sidewall. Additionally, the bottom structural member may further comprise a bottom surface comprising at least one dimple extending inwardly from the bottom surface. Furthermore, the middle structural member may comprise a fluid. Also, each of the top structural member and the bottom structural member may comprise metallic material. The artificial disc may further comprise a gap between a bottom surface of the female cavity of the middle structural member and a top surface of the bottom structural member when the middle structural member is seated in the bottom structural member.

Another embodiment provides a method of attaching an artificial intervertebral disc to vertebral bodies, wherein the method comprises attaching an upper surface of a superior body component to a superior vertebral body, wherein the superior body component comprises a flanged outer periphery; at least one projection member extending outwardly from the upper surface; and a bowl region connected to the flanged outer periphery of the superior body component, wherein the bowl region comprises a cavity extending inwardly from the upper surface. The method further includes attaching a bottom surface of an inferior body component to an inferior vertebral body, wherein the inferior body component comprises a cavity extending inwardly from an upper surface of the inferior body component; and at least one projection member outwardly extending from the bottom surface. The method further includes inserting a load-bearing component in between the superior body component and the inferior body component, wherein the load-bearing component comprises a flanged outer periphery; and a bowl region connected to the flanged outer periphery of the load-bearing component, wherein the bowl region comprises a cavity extending inwardly from an upper surface of the load-bearing component; wherein the bowl region of the superior body component is dimensioned and configured to fit in the cavity of the load-bearing component, and wherein the bowl region of the load-bearing component is dimensioned and configured to fit in the cavity of the inferior body component.

Additionally, the method may further comprise anchoring the at least one projection member of the superior body component into the superior vertebral body; and anchoring the at least one projection member of the inferior body component into the inferior vertebral body, wherein the superior vertebral body and the inferior vertebral body are oppositely positioned to one another. Preferably, the inferior body component further comprises a sidewall defining an outer boundary of the cavity of the inferior body component, and wherein the sidewall comprises at least one hole extending through an entire thickness of the sidewall. Also, the bottom surface of the inferior body component may comprise at least one dimple extending inwardly from the bottom surface. Furthermore, the load-bearing component may comprise flexible material, and each of the superior body component and the inferior body component may comprise metallic material. Moreover, the method may further comprise creating a gap between a bottom surface of the bowl region of the load-bearing component and a top surface of the cavity of the inferior body component when the load-bearing component is seated in the inferior body component.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 2(A) is a schematic diagram illustrating a perspective view of the superior body component of the artificial intervertebral disc of FIG. 1(A) according to an embodiment herein;

FIG. 2(B) is a schematic diagram illustrating a side view of the superior body component of FIG. 2(A) according to an embodiment herein;

FIG. 2(C) is a schematic diagram illustrating a cross-sectional view cut along sectional line B-B of the superior body component of FIG. 2(B) according to an embodiment herein;

FIG. 2(D) is a schematic diagram illustrating a top view of the superior body component of FIG. 2(A) according to an embodiment herein;

FIG. 2(E) is a schematic diagram illustrating a bottom view of the superior body component of FIG. 2(A) according to an embodiment herein;

FIG. 3(A) is a schematic diagram illustrating a perspective view of the load-bearing component of the artificial intervertebral disc of FIG. 1(A) according to an embodiment herein;

FIG. 3(B) is a schematic diagram illustrating a side view of the load-bearing component of FIG. 3(A) according to an embodiment herein;

FIG. 3(C) is a schematic diagram illustrating a cross-sectional view cut along sectional line C-C of the load-bearing component of FIG. 3(B) according to an embodiment herein;

FIG. 3(D) is a schematic diagram illustrating a top view of the load-bearing component of FIG. 3(A) according to an embodiment herein;

FIG. 3(E) is a schematic diagram illustrating a bottom view of the load-bearing component of FIG. 3(A) according to an embodiment herein;

FIG. 4(A) is a schematic diagram illustrating a perspective view of the inferior body component of the artificial intervertebral disc of FIG. 1(A) according to an embodiment herein;

FIG. 4(B) is a schematic diagram illustrating a side view of the inferior body component of FIG. 4(A) according to an embodiment herein;

FIG. 4(C) is a schematic diagram illustrating a cross-sectional view cut along sectional line D-D of the inferior body component of FIG. 4(B) according to an embodiment herein;

FIG. 4(D) is a schematic diagram illustrating a top view of the inferior body component of FIG. 4(A) according to an embodiment herein;

FIG. 4(E) is a schematic diagram illustrating a bottom view of the inferior body component of FIG. 4(A) according to an embodiment herein; and FIG. 5 is a flow diagram illustrating a preferred method according to an embodiment herein.

DETAILED DESCRIPTION OF PREFERRED EMBODIMENTS

Figure 1A:
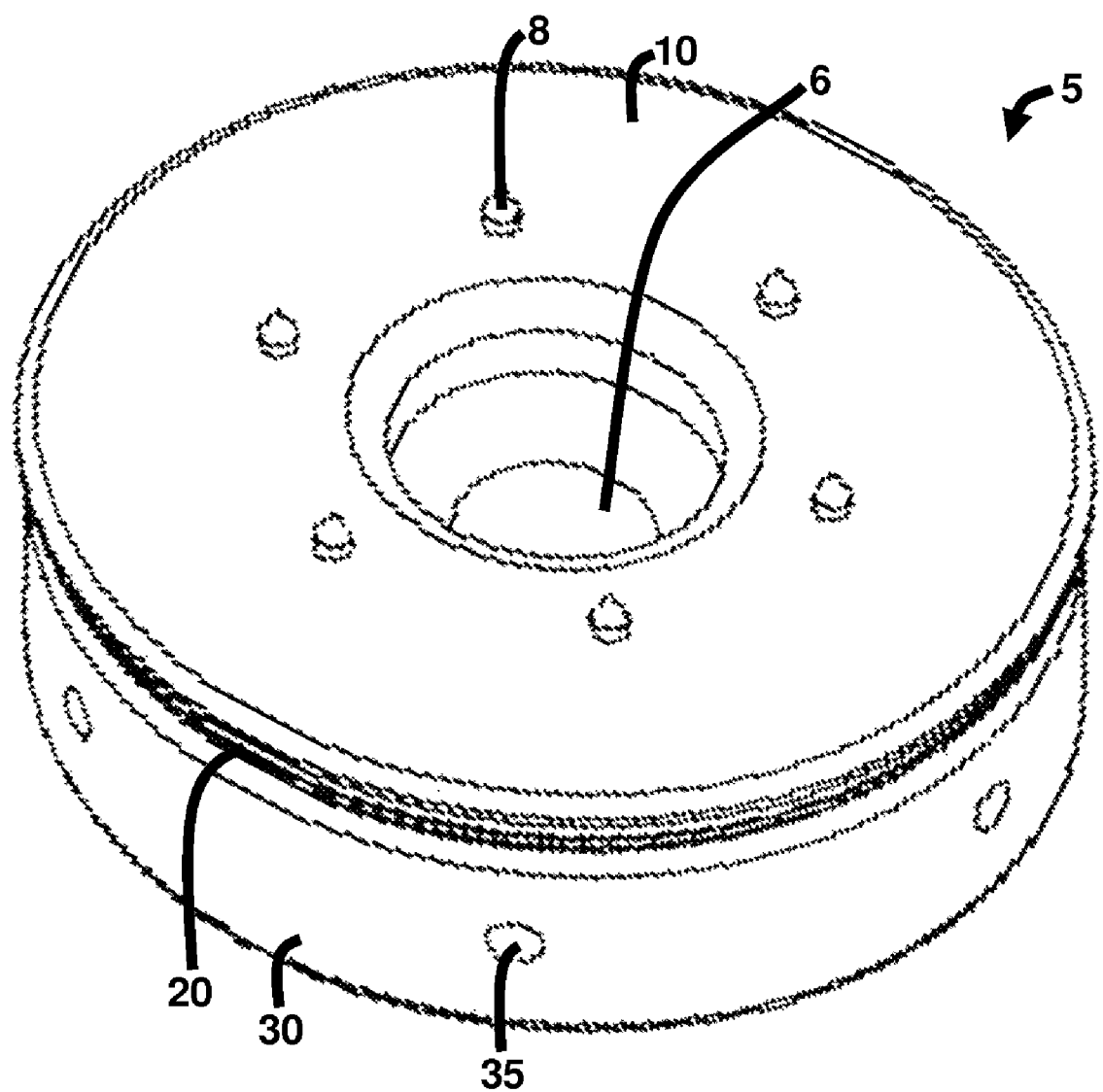
FIG. 1(A) is a schematic diagram illustrating a perspective view of an artificial intervertebral disc according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a novel artificial intervertebral disc capable of controlling both rigid rotation/translation and soft uncontrolled spring/damping motion. The embodiments herein achieve this by providing a novel artificial intervertebral disc that includes three components arranged in a stacked configuration including a load-bearing element that allows for flexibility in movement of the fused section of the spinal column. Referring now to the drawings, and more particularly to FIGS. 1(A) through 5, where similar reference characters denote corresponding features consistently throughout the figures, there are shown preferred embodiments.

FIGS. 1(A) through 1(E) are schematic diagrams illustrating various views of an artificial intervertebral disc 5 according to an embodiment herein. The disc 5 comprises three main independent structural components: a top component (superior body) 10, a middle component (load-bearing element) 20, and a bottom component (inferior body) 30. The superior and inferior bodies 10, 30 each attach to the respective endplates (not shown) of the superior and inferior vertebrae (not shown), respectively. Each body 10, 30 is located on the respective endplate (not shown) with the aid of matched convex/concave surfaces and fixed in place with an anchoring element 8, 18, respectively. The anchoring elements 8, 18 are preferably embodied as protrusions of various geometry, and may comprise porous material, or contain a biological coating, to aid in proper connection with the endplates (not shown). Moreover, the vertebral endplates (not shown) could also be covered with a thin film of various materials. This thin film technology can be used as a divider between the vertebrae (not shown) and either body 10, 20.

As shown in the perspective view of FIG. 1(A), the artificial disc 5 is arranged in a stacked configuration with the load-bearing element 20 positioned in between the superior and inferior bodies 10, 30. Overall, the disc 5 assumes a substantially cylindrical shape (in a three-dimensional plane) and a substantially circular shape (in a two-dimensional plane). As further illustrated in FIG. 1(A), the superior body 10 includes a cavity 6 preferably configured in the center of the superior body 10. Moreover, the inferior body 30 may contain at least one hole 35.

Figure 1B:
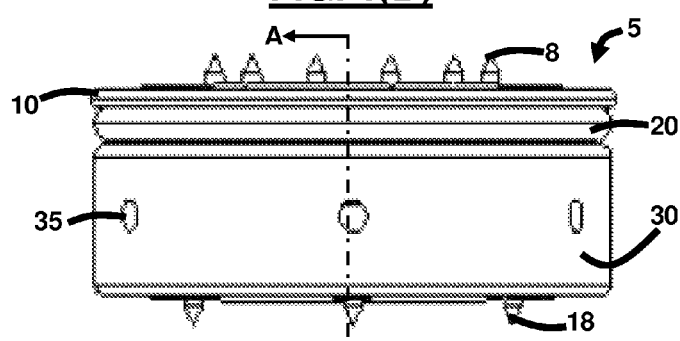
FIG. 1(B) is a schematic diagram illustrating a side view of the artificial intervertebral disc of FIG. 1(A) according to an embodiment herein.

FIG. 1(B) is a schematic diagram illustrating a side view of the artificial intervertebral disc 5 of FIG. 1(A) according to an embodiment herein. This view further illustrates the overall cylindrical shape of the disc 5 and illustrates the relative thicknesses of the exposed portions of the superior body 10, load-bearing element 20, and inferior body 30. Additionally, the relative heights of the anchoring elements 8, 18 outwardly protruding from respective superior and inferior bodies 10, 30 are further illustrated in this view. While the holes 35 are shown to be configured in a substantially middle portion of the inferior body 30, this configuration is merely an example as those skilled in the art could appreciate configuring the holes 35 anywhere on the inferior body 30. Moreover, the holes 35 are shown to be positioned along a plane transverse to the anchoring elements 8, 18.

Figure 1C:
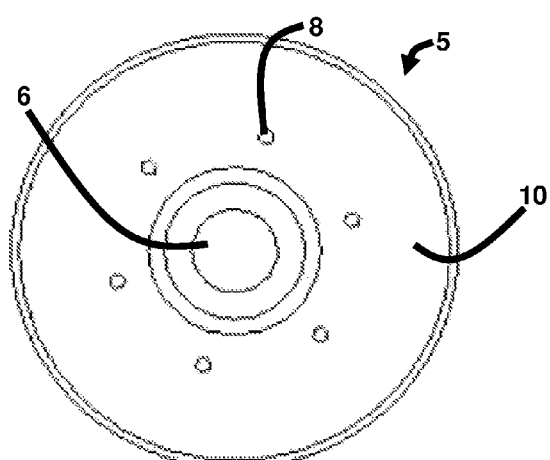
FIG. 1(C) is a schematic diagram illustrating a top view of the artificial intervertebral disc of FIG. 1(A) according to an embodiment herein.
Figure 1D:
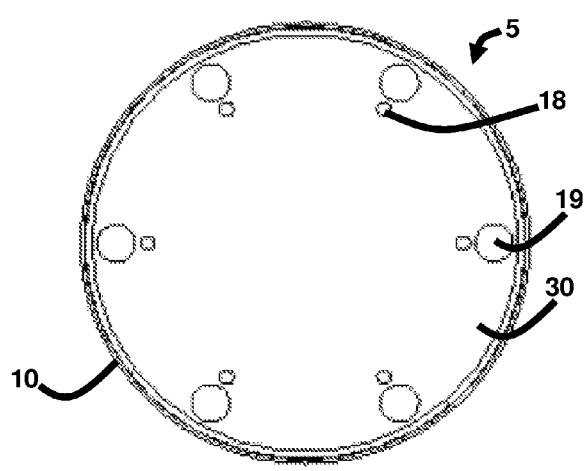
FIG. 1(D) is a schematic diagram illustrating a bottom view of the artificial intervertebral disc of FIG. 1(A) according to an embodiment herein.

FIG. 1(C) is a schematic diagram illustrating a top view of the artificial intervertebral disc 5 of FIG. 1(A) according to an embodiment herein. In this view, which generally shows the superior body 10, the anchoring elements 8 are shown to be arranged in a substantially circular configuration around the cavity 6, which is centrally located in the superior body 10. FIG. 1(D) is a schematic diagram illustrating a bottom view of the artificial intervertebral disc 5 of FIG. 1(A) according to an embodiment herein. In this view, which generally shows the inferior body 30, the anchoring elements 18 are shown to be arranged in a substantially circular configuration around the outer periphery of the inferior body 30. Furthermore, a plurality of dimples 19 are preferably configured next to each anchoring element 18. According to one embodiment, the outer circumference of the load-bearing element 20 and inferior body 30 are substantially equivalent while the outer circumference of the superior body 10 is slightly larger than the outer circumference of the load-bearing element 20 and inferior body 30, which can best be seen in FIGS. 1(B), 1(D), and 1(E). In alternative embodiments, the outer circumference of the superior body 10, load-bearing element 20, and inferior body 30 are substantially equivalent.

Figure 1E:
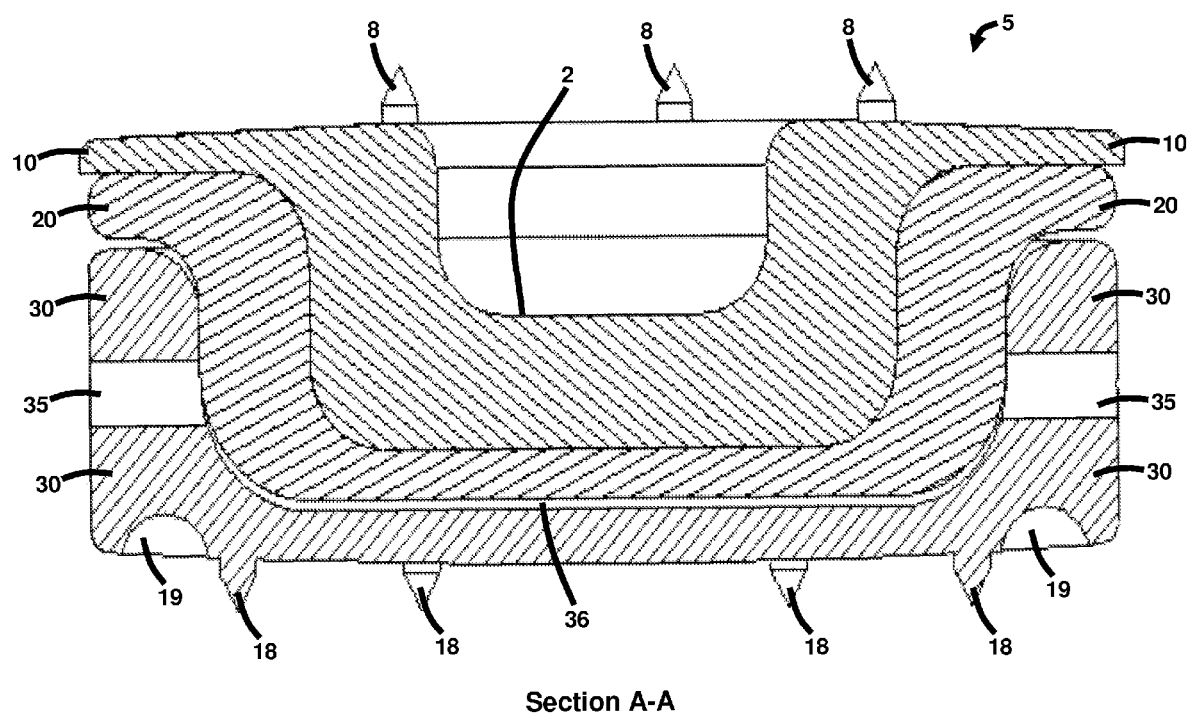
FIG. 1(E) is a schematic diagram illustrating a cross-sectional view cut along sectional line A-A of the artificial intervertebral disc of FIG. 1(A) according to an embodiment herein.

FIG. 1(E) is a schematic diagram illustrating a cross-sectional view cut along sectional line A-A of the artificial intervertebral disc 5 of FIG. 1(A) according to an embodiment herein. As further described below, each of the superior body 10, load-bearing element 20, and inferior body 30 are configured as cascading cup/bowl like structures such that the stacked configuration of the superior body 10 is positioned above and sitting in the load-bearing component 20, which is positioned above and sitting in the inferior body 30. The bottom 2 of the cavity 6 of the superior body 10 may be packed with bone, tissue, or blood to allow for enhanced grafting with the superior endplate (not shown). Furthermore, the depth of the dimples 19 are illustrated. As shown, the anchoring elements 8, 18 may be configured as post-like structures, which may have tips configured to allow for better attachment to the endplates (not shown) of the vertebrae (not shown). A gap 36 preferably exists between the load-bearing element 20 and the inferior body 30, wherein the holes 35 connect to this gap 36. When the disc 5 is attached to the vertebrae endplates (not shown), blood may fill the gap 36, whereby the blood enters the gap 36 via the holes 35.

FIGS. 2(A) through 2(E) are schematic diagrams illustrating various views of the superior body component 10 of the artificial intervertebral disc 5 of FIG. 1(A) according to an embodiment herein. The superior body 10 is preferably embodied in a cup/bowl like configuration having a generally centered bowl region 4, defined by an inner cavity 6, and an outer flanged lip 3.

The anchoring elements 8 are raised and extend in a direction opposite to the bowl region 4. Furthermore, the relative thickness of the outer flanged lip 3 is substantially smaller than the thickness of the bowl region 4. The upper inner portion 38a of the bowl region 4 is outwardly curved to allow for a gradual connection between the flanged lip 3 and the inner cavity 6 of the bowl region 4. Furthermore, the upper outer portion 38b of the bowl region 4 is inwardly curved (to match the curve of the upper inner portion 38a), which serves as a gradual connection to the undersurface 7 of the flanged lip 3. Moreover, the lower outer portion 39b is also outwardly curved and the lower inner portion 39a.

FIG. 2(C) is a schematic diagram illustrating a cross-sectional view cut along sectional line B-B of the superior body component 10 of FIG. 2(B) according to an embodiment herein. This view more clearly reveals the relative depth of the cavity 6, which terminates with a generally flat bottom portion 2 of the cavity 6, which defines the inner configuration of the bowl region 4. FIG. 2(D) is a schematic diagram illustrating a top view of the superior body component 10 of FIG. 2(A) according to an embodiment herein. Here, the anchoring elements 8 are shown to project from a top surface 40 of the flanged lip 3. The edge 42 of the top surface 40 may be outwardly curved to provide a more contoured shape to the superior body component 10. FIG. 2(E) is a schematic diagram illustrating a bottom view of the superior body component 10 of FIG. 2(A) according to an embodiment herein. The outer portion of the bowl region 4 also comprises a generally flat bottom 41.

FIGS. 3(A) through 3(E) are schematic diagrams illustrating various view of the load-bearing component 20 of the artificial intervertebral disc 5 of FIG. 1(A) according to an embodiment herein. The load-bearing component 20 is preferably embodied in a cup/bowl like configuration having a generally centered bowl region 24, defined by an inner cavity 23, and an outer flanged lip 26. Furthermore, the relative thickness of the outer flanged lip 26 is substantially smaller than the thickness of the bowl region 24. The upper inner portion 28a of the bowl region 24 is outwardly curved to allow for a gradual connection between the flanged lip 26 and the inner cavity 23 of the bowl region 24. Furthermore, the upper outer portion 28b of the bowl region 24 is inwardly curved (to match the curve of the upper inner portion 28a), which serves as a gradual connection to the undersurface 27 of the flanged lip 26. Moreover, the lower outer portion 29b is also outwardly curved and the lower inner portion 29a.

FIG. 3(C) is a schematic diagram illustrating a cross-sectional view cut along sectional line C-C of the load-bearing component 20 of FIG. 3(B) according to an embodiment herein. This view more clearly reveals the relative depth of the cavity 23, which terminates with a generally flat bottom portion 22 of the cavity 23, which defines the inner configuration of the bowl region 24. The flanged lip 26 comprises a generally flat upper surface 43 with a generally outwardly curved outer edge 45. The undersurface 27 of the flanged lip 26 also has a generally outwardly curved outer edge 47. The edges 45, 47 provide a more contoured shape to the load-bearing element 20.

FIG. 3(D) is a schematic diagram illustrating a top view of the load-bearing component 20 of FIG. 3(A) according to an embodiment herein. Here, the top surface 43 of the flanged lip 26 is shown terminating with the outer edge 45, and operatively connected, via the curved surfaces 28a, 29a, to the bottom portion 22 of the cavity 23. FIG. 3(E) is a schematic diagram illustrating a bottom view of the load-bearing component 20 of FIG. 3(A) according to an embodiment herein. The outer portion of the bowl region 24 also comprises a generally flat bottom 44 that connects to the curved surface 29b, which connects to the curved surface 28b, which then connects to the undersurface 27 of the flanged lip 26, which terminates with the outer edge 47.

FIGS. 4(A) through 4(E) are schematic diagrams illustrating various views of the inferior body component 30 of the artificial intervertebral disc 5 of FIG. 1(A) according to an embodiment herein. The inferior body 30 is preferably embodied in a cup/bowl like configuration having a generally centered inner cavity 33, and a sidewall 34. The holes 35 are configured so as to extend through the entire thickness of the sidewall 34. The anchoring elements 18 are raised and extend from the bottom surface 37 of the inferior body 30 and in a direction transverse to the holes 35. Furthermore, the relative thickness of the sidewall 34 is substantially smaller than the diameter of the inner cavity 33. The upper surface 36 of the inferior body 30 is substantially flat and terminates with a generally outwardly curved edge 48a. The upper inner portion 49 of the inner cavity 33 is outwardly curved to allow for a gradual connection between the upper surface 36 of the sidewall 34 and the inner cavity 33. Furthermore, the lower outer edge 48b of the bottom surface 37 is outwardly curved. The edges 48a, 48b provide for a contoured shape of the inferior body component 30. Moreover, the lower inner portion 50 of the inner cavity 33 is also inwardly curved to provide a further sloped surface terminating with a generally flat bottom portion 32 of the cavity 33

FIG. 4(C) is a schematic diagram illustrating a cross-sectional view cut along sectional line D-D of the inferior body component 30 of FIG. 4(B) according to an embodiment herein. This view more clearly reveals the relative depth of the cavity 33, which terminates with the generally flat bottom portion 32 of the cavity 33. FIG. 4(D) is a schematic diagram illustrating a top view of the inferior body component 30 of FIG. 4(A) according to an embodiment herein, which further illustrates the various curved surfaces 48a, 49, 50 and the generally flat surfaces 36, 32. FIG. 4(E) is a schematic diagram illustrating a bottom view of the inferior body component 30 of FIG. 4(A) according to an embodiment herein. Here, the anchoring elements 18 are shown to project from the bottom surface 37 of the inferior body 30. Again, the edge 48b of the bottom surface 37 may be outwardly curved to provide a more contoured shape to the inferior body component 30. Furthermore, the dimples 19 are shown in FIG. 4(E) being configured next to the anchoring elements 18, wherein the anchoring elements 18 and dimples 19 may be arranged in a generally circumferential configuration with respect to the center of the bottom surface 37 of the inferior body component 30.

FIG. 5, with reference to FIGS. 1(A) through 4(E), is a flow diagram illustrating a method of attaching an artificial intervertebral disc 5 to vertebral bodies (not shown) according to an embodiment, wherein the method comprises attaching (51) an upper surface 40 of a superior body component 10 to a superior vertebral body (not shown), wherein the superior body component 10 comprises a flanged outer periphery 3; at least one projection member 8 extending outwardly from the upper surface 40; and a bowl region 4 connected to the flanged outer periphery 3 of the superior body component 10, wherein the bowl region 4 comprises a cavity 6 extending inwardly from the upper surface 40. The method further includes attaching (52) a bottom surface 37 of an inferior body component 30 to an inferior vertebral body (not shown), wherein the inferior body component 30 comprises a cavity 33 extending inwardly from an upper surface 36 of the inferior body component 30; and at least one projection member 18 outwardly extending from the bottom surface 37. The method further includes inserting (53) a load-bearing component 20 in between the superior body component 10 and the inferior body component 30, wherein the load-bearing component 20 comprises a flanged outer periphery 26; and a bowl region 24 connected to the flanged outer periphery 26 of the load-bearing component 20, wherein the bowl region 24 comprises a cavity 23 extending inwardly from an upper surface 43 of the load-bearing component 20; wherein the bowl region 4 of the superior body component 10 is dimensioned and configured to fit in the cavity 23 of the load-bearing component 20, and wherein the bowl region 24 of the load-bearing component 20 is dimensioned and configured to fit in the cavity 33 of the inferior body component 30.

Additionally, the method may further comprise anchoring the at least one projection member 8 of the superior body component 10 into the superior vertebral body (not shown); and anchoring the at least one projection member 18 of the inferior body component 30 into the inferior vertebral body (not shown), wherein the superior vertebral body (not shown) and the inferior vertebral body (not shown) are oppositely positioned to one another. Preferably, the inferior body component 30 further comprises a sidewall 34 defining an outer boundary of the cavity 33 of the inferior body component 30, and wherein the sidewall 34 comprises at least one hole 35 extending through an entire thickness of the sidewall 34.

Also, the bottom surface 37 of the inferior body component 30 may comprise at least one dimple 19 extending inwardly from the bottom surface 37. Furthermore, the load-bearing component 20 may comprise flexible material, and each of the superior body component 10 and the inferior body component 30 may comprise metallic material. Moreover, the method may further comprise creating a gap 36 between a bottom surface 44 of the bowl region 24 of the load-bearing component 20 and a top surface 32 of the cavity 33 of the inferior body component 30 when the load-bearing component 20 is seated in the inferior body component 30.

Preferably, the load-bearing component 20 may comprise flexible materials, polymers, ceramics, metals, hydro gels, liquids, etc. The superior and inferior bodies 10, 30 are paired male and female shaped respectively to constrain the load-bearing component 20. Additionally, the shape of the bowl region 4 of the superior body component 10 matches the shape of the cavity 23 of the load-bearing component 20. Moreover, the shape of the bowl region 24 of the load-bearing component 20 matches the shape of the cavity 33 of the inferior body component 30. However, a gap 36 (shown in FIG. 1(E)) may exist between the bottom surface 44 of the load-bearing component 20 and generally flat bottom portion 32 and lower inner portion 50 of the cavity 33 of the inferior body component 30. In another embodiment, the superior body component 10 may also include holes (not shown) on the walls of the bowl region 4. These holes along with holes 35 may let blood or other body fluid flow in and out of the disc 5 equilibrated and based on intra-disc pressure. The fluid would act as a natural damper of the disc 5. In this manner, the load-bearing component 20 of the disc 5 acts as a paired spring/damper connector.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An artificial intervertebral disc comprising:
    a first body component having a first body upper surface, said first body component comprising:
        a flanged outer periphery;
        at least one first body projection member extending outwardly from said first body upper surface; and
        a first bowl region connected to said flanged outer periphery of said first body component, wherein said first bowl region comprises a first body cavity extending inwardly from said first body upper surface;
    a second body component having a second body upper surface, said second body component comprising:
        a flanged outer periphery; and
        a second bowl region connected to said flanged outer periphery of said second body component, wherein said second bowl region comprises a second body cavity extending inwardly from said second body upper surface;
    a third body component having a third body upper surface and a third body bottom surface, said third body component comprising:
        a third body cavity extending inwardly from said third body upper surface;
        at least one third body projection member outwardly extending from said third body bottom surface; and
        a sidewall defining an outer boundary of said third body cavity, wherein said sidewall comprises at least one hole extending through an entire thickness of said sidewall;
    wherein said first bowl region fits in said second body cavity, and
    wherein said second bowl region fits in said third body cavity.

2. The artificial disc of claim 1, wherein each of said at least one first body projection member and said at least one third body projection member respectively anchor into oppositely positioned vertebral bodies.

3. The artificial disc of claim 1, wherein said third body bottom surface comprises at least one dimple extending inwardly from said third body bottom surface.

4. The artificial disc of claim 1, wherein said second body component comprises flexible material.

5. The artificial disc of claim 1, wherein each of said first body component and said third body component comprises metallic material.

6. An artificial intervertebral disc comprising:
    a first body component having a first body upper surface, said first body component comprising:
        a flanged outer periphery;
        at least one first body projection member extending outwardly from said first body upper surface; and
        a first bowl region connected to said flanged outer periphery of said first body component, wherein said first bowl region comprises a first body cavity extending inwardly from said first body upper surface;
    a second body component having a second body upper surface, said second body component comprising:
        a flanged outer periphery; and
        a second bowl region connected to said flanged outer periphery of said second body component, wherein said second bowl region comprises a second body cavity extending inwardly from said second body upper surface;
    a third body component having a third body upper surface and a third body bottom surface, said third body component comprising:
        a third body cavity extending inwardly from said third body upper surface; and
        at least one third body projection member outwardly extending from said third body bottom surface,
    a gap between a bottom surface of said second body cavity and a top surface of said third body cavity when said second body component is seated in said third body component,
    wherein said first bowl region fits in said second body cavity, and
    wherein said second bowl region fits in said third body cavity.

7. The artificial disc of claim 6, wherein said third body component further comprises a sidewall defining an outer boundary of said third body cavity, and wherein said sidewall comprises at least one hole extending through an entire thickness of said sidewall.

8. An artificial intervertebral disc comprising a plurality of separate structural members arranged in a stacked configuration, wherein each structural member comprises a female cavity having a unique size compared with the female cavities of the other structural members, wherein a top and middle structural member comprise male bodies defined by outer edges of the respective female cavities of the top and middle structural members, wherein the male body of said top structural member sits in the female body of said middle structural member, wherein the male body of said middle structural member sits in the female body of a bottom structural member, wherein each of the top and bottom structural member comprise at least one projecting member outwardly extending therefrom, and wherein said bottom structural member further comprises a sidewall defining an outer boundary of the female cavity of said bottom structural member, and wherein said sidewall comprises at least one hole extending through an entire thickness of said sidewall.

9. The artificial disc of claim 8, wherein said each at least one projection member of the top and bottom structural members respectively anchor into oppositely positioned vertebral bodies.

10. The artificial disc of claim 8, wherein said bottom structural member further comprises a bottom surface comprising at least one dimple extending inwardly from said bottom surface.

11. The artificial disc of claim 8, wherein said middle structural member comprises a fluid.

12. The artificial disc of claim 8, wherein each of said top structural member and said bottom structural member comprises metallic material.

13. An artificial intervertebral disc comprising a plurality of separate structural members arranged in a stacked configuration, wherein each structural member comprises a female cavity having a unique size compared with the female cavities of the other structural members, wherein a top and middle structural member comprise male bodies defined by outer edges of the respective female cavities of the top and middle structural members, wherein the male body of said top structural member sits in the female body of said middle structural member, wherein the male body of said middle structural member sits in the female body of a bottom structural member, wherein each of the top and bottom structural member comprise at least one projecting member outwardly extending therefrom, and wherein a gap exists between a bottom surface of the female cavity of said middle structural member and a top surface of said bottom structural member when said middle structural member is seated in said bottom structural member.

14. The artificial disc of claim 13, wherein said bottom structural member further comprises a sidewall defining an outer boundary of the female cavity of said bottom structural member, and wherein said sidewall comprises at least one hole extending through an entire thickness of said sidewall.

15. A method of attaching an artificial intervertebral disc to vertebral bodies, said method comprising:
attaching an upper surface of a superior body component to a superior vertebral body, wherein said superior body component comprises:
a flanged outer periphery;
at least one projection member extending outwardly from said upper surface; and
a bowl region connected to said flanged outer periphery of said superior body component, wherein said bowl region comprises a cavity extending inwardly from said upper surface;
attaching a bottom surface of an inferior body component to an inferior vertebral body, wherein said inferior body component comprises:
a cavity extending inwardly from an upper surface of said inferior body component;
at least one projection member outwardly extending from said bottom surface; and
a sidewall defining an outer boundary of said cavity of said inferior body component, wherein said sidewall comprises at least one hole extending through an entire thickness of said sidewall;
inserting a load-bearing component in between said superior body component and said inferior body component, wherein said load-bearing component comprises:
a flanged outer periphery; and
a bowl region connected to said flanged outer periphery of said load-bearing component, wherein said bowl region comprises a cavity extending inwardly from an upper surface of said load-bearing component;
wherein said bowl region of said superior body component fits in said cavity of said load-bearing component, and
wherein said bowl region of said load-bearing component fits in said cavity of said inferior body component.

16. The method of claim 15, further comprising:
anchoring said at least one projection member of said superior body component into said superior vertebral body; and
anchoring said at least one projection member of said inferior body component into said inferior vertebral body, wherein said superior vertebral body and said inferior vertebral body are oppositely positioned to one another.

17. The method of claim 15, wherein said bottom surface of said inferior body component comprises at least one dimple extending inwardly from said bottom surface.

18. The method of claim 15, wherein said load-bearing component comprises flexible material, and wherein each of said superior body component and said inferior body component comprises metallic material.

19. A method of attaching an artificial intervertebral disc to vertebral bodies, said method comprising:
attaching an upper surface of a superior body component to a superior vertebral body, wherein said superior body component comprises:
a flanged outer periphery;
at least one projection member extending outwardly from said upper surface; and
a bowl region connected to said flanged outer periphery of said superior body component, wherein said bowl region comprises a cavity extending inwardly from said upper surface;
attaching a bottom surface of an inferior body component to an inferior vertebral body, wherein said inferior body component comprises:
a cavity extending inwardly from an upper surface of said inferior body component;
at least one projection member outwardly extending from said bottom surface; and
a sidewall defining an outer boundary of said cavity of said inferior body component, wherein said sidewall comprises at least one hole extending through an entire thickness of said sidewall;
inserting a load-bearing component in between said superior body component and said inferior body component, wherein said load-bearing component comprises:
a flanged outer periphery; and
a bowl region connected to said flanged outer periphery of said load-bearing component, wherein said bowl region comprises a cavity extending inwardly from an upper surface of said load-bearing component;

creating a gap between a bottom surface of said bowl region of said load-bearing component and a top surface of said cavity of said inferior body component when said load-bearing component is seated in said inferior body component, wherein said bowl region of said superior body component fits in said cavity of said load-bearing component, and wherein said bowl region of said load-bearing component fits in said cavity of said inferior body component.

20. The method of claim 19, wherein said inferior body component further comprises a sidewall defining an outer boundary of said cavity of said inferior body component, and wherein said sidewall comprises at least one hole extending through an entire thickness of said sidewall.

* * * * *